United States Patent
Wang et al.

(10) Patent No.: US 9,567,620 B2
(45) Date of Patent: Feb. 14, 2017

(54) RESISTIVE SENSOR BASED ON CONDUCTIVITY CHANGE OF CONDUCTIVE POLYMER AND MEASURING METHOD THEREOF

(71) Applicant: National Tsing Hua University, Hsinchu (TW)

(72) Inventors: Yu-Lin Wang, Hsinchu (TW); Kuan-Chung Fang, Hsinchu (TW); Chia-Ho Chu, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 129 days.

(21) Appl. No.: 14/623,867

(22) Filed: Feb. 17, 2015

(65) Prior Publication Data

US 2016/0115516 A1 Apr. 28, 2016

(30) Foreign Application Priority Data

Oct. 28, 2014 (TW) .............................. 103137158 A

(51) Int. Cl.
| | |
|---|---|
| G01N 27/327 | (2006.01) |
| C12Q 1/00 | (2006.01) |
| C12Q 1/28 | (2006.01) |
| G01N 27/04 | (2006.01) |

(52) U.S. Cl.
CPC ............... *C12Q 1/005* (2013.01); *C12Q 1/28* (2013.01); *C12Q 2527/125* (2013.01); *G01N 27/04* (2013.01)

(58) Field of Classification Search
CPC ................ G01N 27/02; G01N 27/04; G01N 27/327–27/3272
See application file for complete search history.

(56) References Cited

U.S. PATENT DOCUMENTS

| 5,202,261 A | 4/1993 | Musho et al. | |
|---|---|---|---|
| 5,312,762 A * | 5/1994 | Guiseppi-Elie | ........... C08F 8/00 205/778 |
| 5,334,296 A * | 8/1994 | Henkens | ................ C12Q 1/003 204/403.14 |

FOREIGN PATENT DOCUMENTS

| JP | 60095343 A * | 5/1985 | ............. G01N 33/66 |
|---|---|---|---|
| RO | 126672 A2 * | 9/2011 | ............... C12Q 1/26 |

OTHER PUBLICATIONS

Derwent English langauge abstract of Gutt et al. RO 126672 A2, patent published Sep. 30, 2011.*

(Continued)

*Primary Examiner* — Alexander Noguerola
(74) *Attorney, Agent, or Firm* — Muncy, Geissler, Olds & Lowe, P.C.

(57) ABSTRACT

A resistive sensor for an analyte comprises a substrate, a conductive polymer layer and an oxidase layer. Hydrogen peroxide is produced via the reaction between analyte and oxidase when a liquid sample is applied to the sensor of the present invention. The produced hydrogen peroxide can oxidize peroxidase, which can be reduced by oxidizing the conductive polymer, thus resulting in decreased conductivity of the conductive polymer for determining the analyte concentration in the liquid sample. The present invention may be used for developing miniaturized and disposable electronic microsensors with high sensitivity and fast response, which can detect analyte level in typical physiological environment for routine monitoring.

13 Claims, 6 Drawing Sheets

(56) References Cited

OTHER PUBLICATIONS

Derwent English language abstract of Hiratsuka et al. JP 60095343 A, patent published May 28, 1985.*
English language translation of Hiratsuka et al. JP 60095343 A, patent published May 28, 1985.*
English language translation of Gutt et al. RO 126672 A2, translation dated Aug. 2016.*
Kuan-Chung Fang, et al., "Cost-effective and highly sensitive cholesterol microsensors with fast response based on the enzyme-induced conductivity change of polyaniline", Applied Physics Letters 105, 113304 (2014), 6 pages.

* cited by examiner

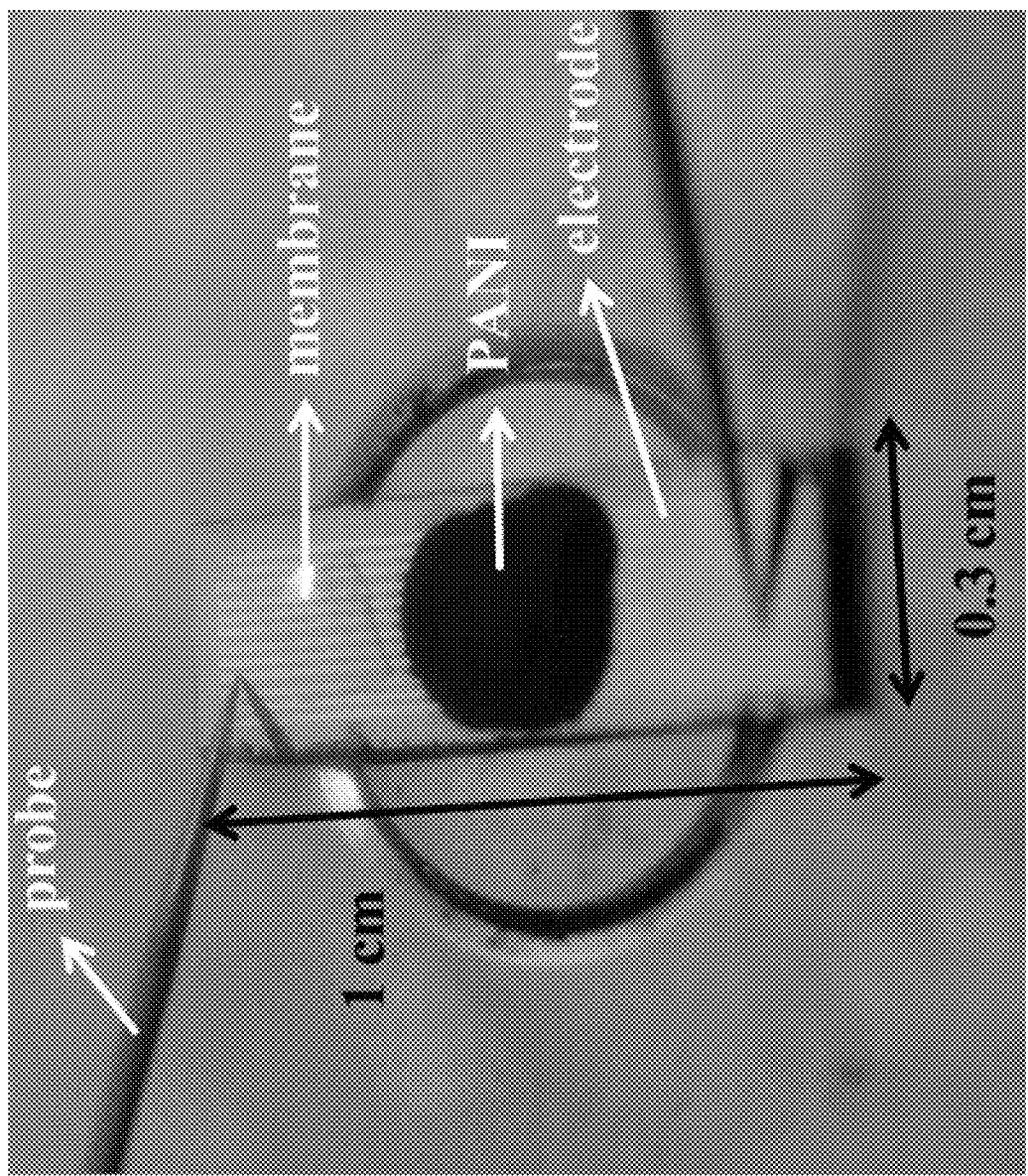

RESISTIVE SENSOR BASED ON CONDUCTIVITY CHANGE OF CONDUCTIVE POLYMER AND MEASURING METHOD THEREOF

BACKGROUND OF THE INVENTION

1. Field of the Invention

The present invention relates to resistive sensor, particularly to resistive cholesterol sensor based on conductivity change of the conductive polymer.

2. Description of the Prior Art

Cholesterol detection draws a lot of attention because the abnormal cholesterol level may indicate clinical disorders such as heart disease, hypertension, arteriosclerosis, and cerebral thrombosis etc. According to the report published by World Health Organization, 17.3 million people were estimated that died in cardiovascular diseases in 2008 globally and the death toll keeps increasing annually. It is crucial to monitor cholesterol level in blood for estimating the potential risk of cardiovascular disease and preventing deaths from the disease. Many researches have been devoted in the development of cholesterol sensors.

There is an increasing demand on for cheap and disposable electronic cholesterol sensors for the point-of-care health monitoring. Electronic biosensors, such as electrochemical, field-effect-transistor-based, or resistive biosensors are cheap and small thanks to the mature microfabrication techniques. Therefore, it is possible to develop miniaturized and disposable electronic microsensors with high sensitivity and fast response, which can detect cholesterol level in typical physiological environment for routine monitoring.

Most electrochemical sensors detect cholesterol by voltammetry, in which, cholesterol oxidase was immobilized on electrode and oxidize cholesterol into cholestenone.

The reduced cholesterol oxidase will then be oxidized via the electrode and therefore the catalysis of the enzyme reaction can continue. Different materials were used for the electrode to enhance charge transfer rate or to immobilize cholesterol oxidase (ChOx) more efficiently.

Multiwall carbon nanotubes (MWCNT), conducting polymer-MWCNT composite, MWCNT/Screen Printed Carbon Electrode (SPCE), conducting polymer, graphene, or nano structured metal oxides such as ZnO nanorods (NRs), ZnO nano sphere, anatase-titanium dioxide and $SnO_2$ nanoparticles were reported for electrode materials which can improve the charge transfer rate or ChOx immobilization. ChOx-immobilized ZnO NR-gated field-effect-transistor (FET) was also reported to be able to sensitively detect cholesterol.

However, compared to resistive biosensors, electrochemical sensors and FET-based sensors are more complicated in sensor design or the measurement system. The resistive type of sensors exhibits conductivity change, which is directly proportional to the cholesterol level, and therefore is much simpler for device fabrication and signal measurements.

SUMMARY OF THE INVENTION

One objective of the present invention is directed to developing resistive cholesterol sensors with simplicity, effective cost and high sensitivity.

A resistive cholesterol sensor comprises a substrate, a conductive polymer layer and a cholesterol oxidase layer. The conductive polymer layer is configured on the substrate and provided with a peroxidase configured thereon, and the peroxidase is used for oxidizing the conductive polymer layer so that a conductivity of the conductive polymer layer is decreased after applying an analyte, wherein a conductivity change of the conductive polymer layer is related to a concentration of the analyte, wherein the conductive polymer layer is essentially made of polyaniline or derivatives thereof. The cholesterol oxidase layer is configured on the conductive polymer layer and provided with a cholesterol oxidase configured thereon, wherein the cholesterol oxidase is separately configured from the peroxidase and used for oxidizing the analyte to generate a hydrogen peroxide so that the peroxidase is oxidized by the hydrogen peroxide.

According to another embodiment of the present invention, a measuring method of cholesterol using the above-mentioned resistive cholesterol sensor comprises providing the above-mentioned resistive cholesterol sensor; applying a liquid sample with cholesterol to the resistive cholesterol sensor so that the conductive polymer layer is covered with the liquid sample and the conductivity of the conductive polymer layer is lowered due to oxidation of the conductive polymer by combined reaction of cholesterol, CHOx and peroxidase; and calculating the concentration of the cholesterol in the liquid sample based on the conductivity change rate of the conductive polymer before and after the liquid sample is applied to the conductive polymer.

Other advantages of the present invention will become apparent from the following descriptions taken in conjunction with the accompanying drawings wherein certain embodiments of the present invention are set forth by way of illustration and examples.

BRIEF DESCRIPTION OF THE DRAWINGS

The foregoing aspects and many of the accompanying advantages of this invention will become more readily appreciated as the same becomes better understood by reference to the following detailed descriptions, when taken in conjunction with the accompanying drawings, wherein:

FIG. 1c shows the top view of the photography of a resistive cholesterol sensor coated with PANI;

DESCRIPTION OF THE PREFERRED EMBODIMENT

Figure 1A:
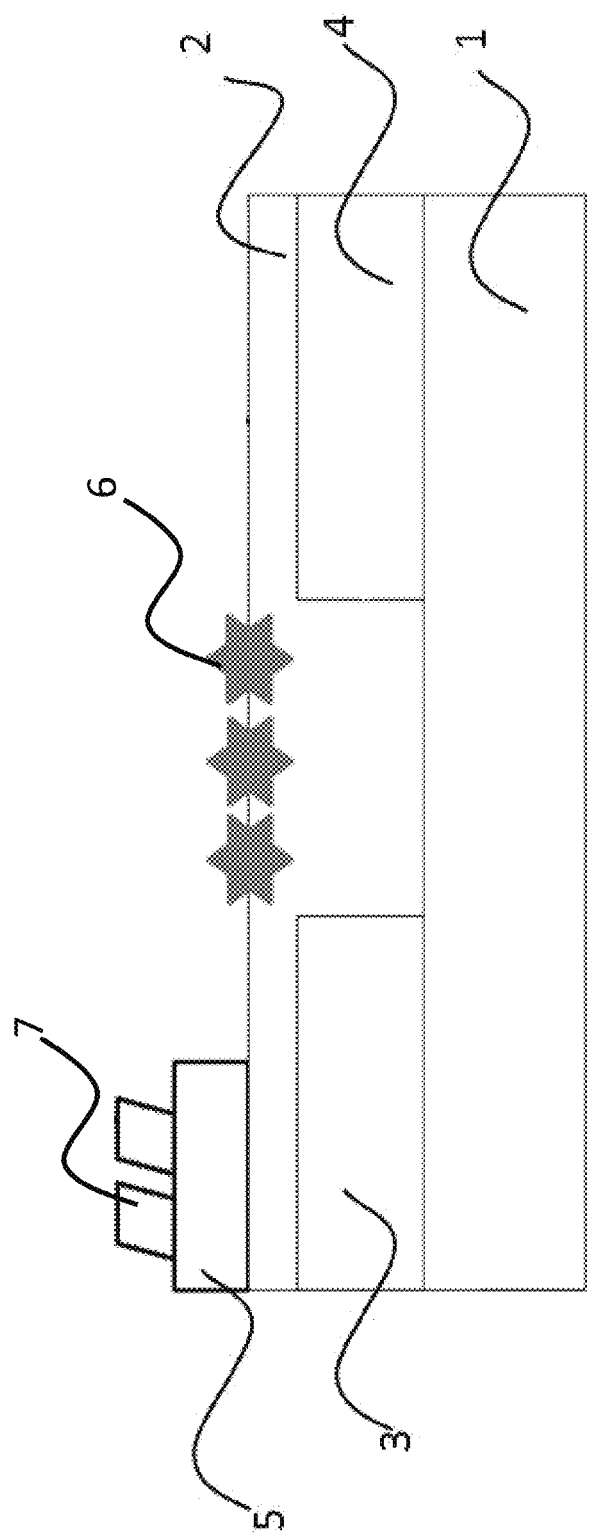
FIG. 1a illustrates a resistive cholesterol sensor according to one embodiment of the present invention.

Referring to FIG. 1a, a resistive cholesterol sensor comprises a substrate 1, a conductive polymer layer 2, a cholesterol oxidase (ChOx) layer 5, a first electrode 3 and a second electrode 4. The conductive polymer layer 2 is configured on the substrate 1 and provided with a peroxidase 6 configured thereon. The peroxidase 6 may include with being limited to horseradish peroxidase (HRP), lactoperoxidase or microperoxidase. The conductive polymer layer 2 is essentially made of a conductive polymer including polyacetylene, polypyrrole, polyparaphenylene, polythiophene, polyfuran, polythianaphthene or polyaniline (PANI). In one preferred embodiment, the conductive polymer may be polyaniline. The surface of the conductive polymer is modified with propane sultone. Wherein the first electrode 3 and the second electrode 4 may be configured underneath a partial area of the conductive polymer layer 2.

It is noted that polyaniline may include derivatives thereof, for example crosslink or non-crosslink forms, soluble or non-soluble forms of derivatives. The polyaniline derivatives may be those composed of aniline having at least one alkyl group, alkenyl group, alkoxy group, alkylthio group, aryl group, aryloxy group, alkylaryl group, arylalkyl group, or alkoxyalkyl group as a substituent group at positions other than the 4th position can be exemplified. An polyaniline derivative having at least one $C_1$ to $C_5$ alkyl group, alkoxy group, or alkoxyalkyl group, a $C_6$ to $C_{10}$ aryl group, as a substituent group, can be preferably exemplified.

In one preferred embodiment, the conductive polymer is pre-treated with acid so as to provide enhanced conductivity. The acid for pretreating the conductive polymer may include without being limited to sulfuric acid, chloric acid and so on. The initial current of the pretreated conductive polymer may range from 10 µA to 1000 µA at constant bias of 100 mV, in terms of about 0.1 mΩ to 10 mΩ or about 0.89 S/cm to 88.89 S/cm. Preferably the initial current of the pretreated conductive polymer may range from 100 µA to 400 µA, in terms of about 1 mΩ to 4 mΩ or about 8.89 S/cm to 35.56 S/cm.

The cholesterol oxidase layer 5 is configured on the substrate 1 and provided with a cholesterol oxidase (ChOx) 7 configured thereon, wherein the cholesterol oxidase 7 is separately configured from the conductive polymer layer 2. The simple process of the sensor fabrication allows the sensor to be cost-effective and disposable usage.

In one embodiment, the cholesterol oxidase may be substituted by other oxidases to detect other analytes. Other oxidases may include without being limited to glucose oxidase, alcohol oxidase, choline oxidase and so on. It should be understood that cholesterol oxidase would be used when cholesterol is the predetermined analyte of interest. However, if a different analyte is of interest, the cholesterol oxidase is replaced by the appropriate oxidase enzyme that interacts with that particular predetermined analyte. For example, if alcohol is the predetermined analyte of interest, a sufficient amount of alcohol oxidase replaces the cholesterol oxidase.

The material of the substrate is not particularly limited in the present invention. In addition, the material and size of the first electrode and the second electrode that achieve conductance and measure are not particularly limited. The electric conductance of the conductive polymer layer may be measured by a sensing element (not shown) electrically connected to the conductive polymer layer.

In one particular embodiment, a cost-effective and highly sensitive cholesterol microsensor, which is consisted of cholesterol oxidase (ChOx), horseradish peroxidase (HRP) and polyaniline (PANI), was developed based on the enzyme-induced conductivity change of PANI with fast response. Hydrogen peroxide is produced via the reaction between cholesterol and ChOx, which was immobilized in a dialysis membrane. The produced hydrogen peroxide can oxidize HRP, which can be reduced by oxidizing PANI, thus resulting in decreased conductivity of the polyaniline thin film. The reduced HRP can be oxidized again by hydrogen peroxide and the cycle of the oxidation/reduction continues until all hydrogen peroxide are reacted, leading to the high sensitivity of the sensor due to the signal contributed from all hydrogen peroxide molecules.

The reactions in our study for cholesterol sensors are shown as followings.

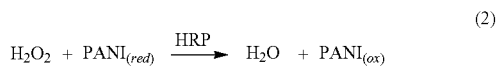

Where the $PANI_{(red)}$ and $PANI_{(ox)}$ represent the reduced and oxidized PANI thin film, respectively. In the present invention, both the generation of hydrogen peroxide from the first reaction and the oxidation of PANI in the second reaction are all spontaneous. Therefore, it is not necessary to apply any external bias to trigger any oxidation or reduction reactions, as most electrochemical sensors did for this sensor, which can avoid any interference from un-necessary oxidation or reduction resulted from external bias. In the meantime, the signal measurement for this sensor becomes easy and straightforward.

In one embodiment, cholesterol is detected near the physiological concentrations ranging from 100 mg/dL to 400 mg/L with the cholesterol sensors. The results show linear relation between cholesterol concentration and the conductivity change of the PANI. The decrease rate of PANI conductance before and after applying the cholesterol may range from 10% to 60%, preferably 20% to 50%. The sensor showed no response to cholesterol when the PANI was standalone without cholesterol oxidase immobilized, indicating that the enzymatic reaction is required for cholesterol detection.

At final step, the concentration of the cholesterol in the liquid sample is calculated based on the conductivity change rate of the conductive polymer before and after the liquid sample is applied to the conductive polymer layer 2. A first conductivity and a second conductivity of the conductive polymer layer are measured, wherein the first conductivity is the conductivity of the conductive polymer layer before applied with the liquid sample with cholesterol and the second conductivity is the conductivity of the conductive polymer layer after applied with the liquid sample with cholesterol, and the conductivity change rate of the conductive polymer is based on the change rate of the first conductivity and the second conductivity. For example, conductivity change rate of the conductive polymer is defined as the differential value between the first and second conductivity divided by the first conductivity.

In one embodiment, the first conductivity and the second conductivity of the conductive polymer layer are measured by applying a bias to the conductive polymer layer and measuring a current of the conductive polymer layer, wherein the conductive polymer layer is electrically connected to the first electrode and the second electrode and the bias is applied to the first electrode and the second electrode.

The present invention has developed an ultra-sensitive hydrogen peroxide microsensor using horseradish peroxidase (HRP)-immobilized polyaniline (PANI) to detect $H_2O_2$ previously. Hydrogen peroxide can oxidize HRP, and then the oxidized HRP can be reduced by oxidizing the highly conductive PANI thin film again. PANI provides an efficient surface for the direct electrochemical reduction of HRP. The oxidized PANI shows a decreased conductivity. The high sensitivity relies on the accumulated conductivity change of PANI by consuming all hydrogen peroxide molecules with PANI via the catalysis effect of HRP, spontaneously.

To accommodate these two reactions, PANI was first spin-coated on Au electrodes on a $Si_3N_4$/Si substrate, followed by being modified with propane sultone (N-Alkylated PANI) to ensure its high conductivity in neutral solution, and then immobilized with HRP. A ChOx-immobilized dialysis membrane was then placed aside the HRP-immobilized PANI for cholesterol detection.

The high sensitivity of this sensor is attributed to the enzymatic signal amplification by accumulating conductance change of the PANI film. In addition, the sensor only requires a small sample volume. The developed cholesterol microsensor has the advantages such as low cost, small size, fast response and ease of operation, which make it a perfect candidate for the routine personal healthcare monitoring.

The present invention is further illustrated by the following working examples, which should not be construed as further limiting.

Polyaniline emeraldine base was purchased from Sigma-Aldrich. 0.3 g of polyaniline emeraldine base powder was dissolved in 5 ml of dimethyl sulfoxide (DMSO) with stirring for 6 hours. The polyaniline solution was then mixed with the same volume of 0.5 M sulfuric acid for 24 hours. The sulfuric acid can increase the conductivity and the stability of the PANI thin film. After that, 1.5 µl of the PANI solution was dropped on a microchip and spin-coated at 1600 rpm for 30 seconds, followed by baking at 60° C. for 30 minutes in air.

The microchip consists of two metal electrodes made by 200Å Ti and 1000Å Au deposited with an e-beam evaporator on a $Si_3N_4$/Si substrate. The length and the width of the Au electrodes are 500 µm and 100 µm, respectively. The separation between the two metal electrodes is 10 µm. The PANI/Au interface was confirmed to be ohmic by measuring the current-voltage characteristics of the device. The PANI-coated device was then held at −0.2 V for 10 minutes followed by being washed with DI water and then immersed into a 1.2 M of NaOH solution for 20 minutes. The device was then dried with nitrogen gas. Propane sultone was dropped on the PANI film and allowed to wait for 8 hours. The device was then washed with DI water to remove the excess propane sultone.

HRP and 1,4-diaminobenzene were purchased from Sigma-Aldrich. The HRP enzyme was prepared in 120 units $cm^{-3}$ in a citrate phosphate buffer solution (pH=5.5), with 25 mM of 1,4-diaminobenzene. The prepared device was then placed in the HRP enzyme solution for 20 minutes, followed by being applied with 0.4 V for 4 minutes. The sensor was then washed with buffer solution to remove unbond HRP.

The ChOx solution was prepared in 22 units/ml in a Phosphate Buffer Saline (PBS) (pH=7.0). The ChOx (Cat. No. 9028-76-6) was purchased from Sigma-Aldrich. A small piece of dialysis membrane (2 mm×2 mm) was then soaked in the ChOx solution for 24 hours at 4° C. The ChOx-immobilized dialysis membrane was then placed aside the HRP-immobilized PANI thin film on the chip. During the detection of cholesterol, the solution is able to cover both the dialysis membrane and the HRP-immobilized PANI.

The current of the sensor was measured at a dc bias of 0.1 V at room temperature using an Agilent B1500 parameter analyzer with the dialysis membrane and the PANI layer exposed to the cholesterol solution.

Different concentrations of cholesterol prepared in citrate PBS buffer solutions (pH=7.0) were directly dropped onto fresh sensors and the currents were measured.

The water-soluble cholesterol was purchased from Sigma-Aldrich. The physiological concentrations of cholesterol, including 100 mg/dL, 150 mg/dL, 200 mg/dL, 250 mg/dL, 300 mg/dL, and 400 mg/dL, in 5 ul, were tested with fresh sensors.

Figure 1B:
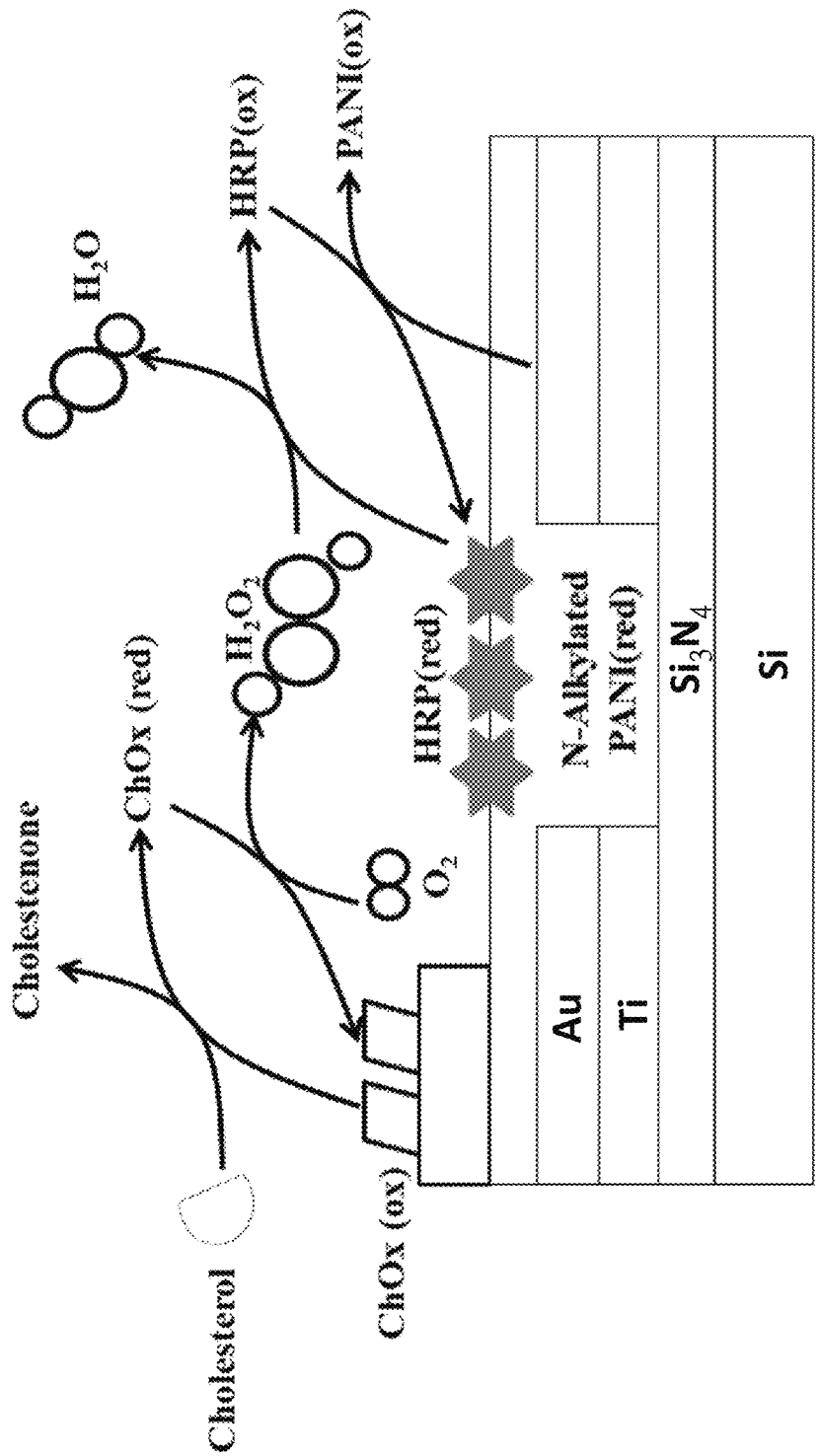
FIG. 1b illustrates a resistive cholesterol sensor using PANI.
Figure 2A:
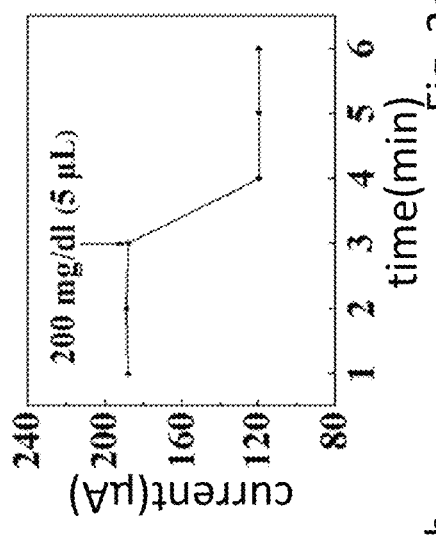
FIGS. 2a to 2f show the real time detection of 5 μl of 100 mg/dL, 150 mg/dL, 200 mg/dL, 250 mg/dL, 300 mg/dL, and 400 mg/dL water-soluble cholesterol, respectively, at a constant bias of 100 mV with fresh sensors.
Figure 2B:
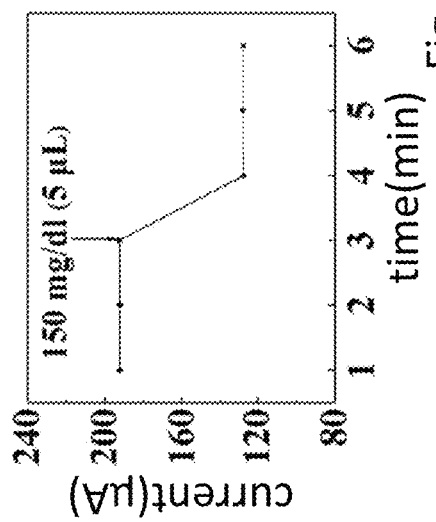
Figure 2C:
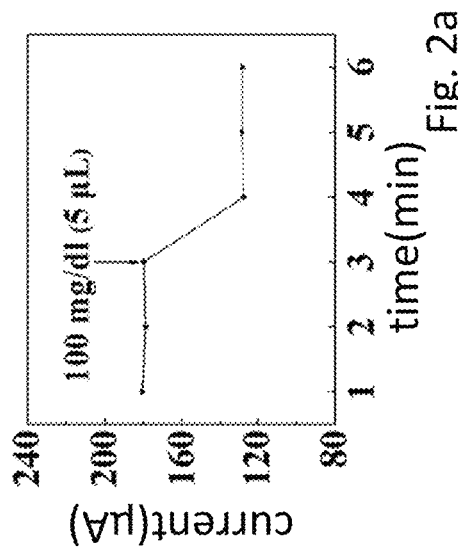
Figure 2D:
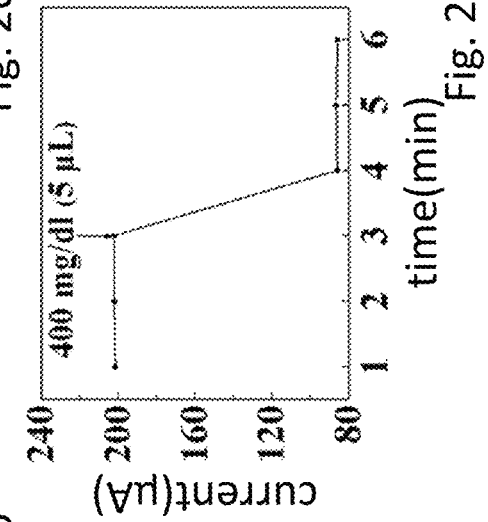
Figure 2E:
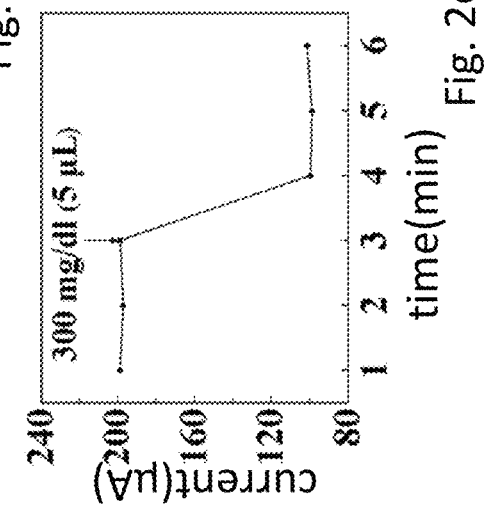
Figure 2F:
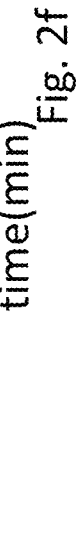

The schematic of the cholesterol sensor and the enzymatic reactions are shown as in FIG. 1b. FIG. 1c shows the top view of the photography of a cholesterol sensor, wherein the detecting element is a probe. A control experiment was also done by placing a dialysis membrane without ChOx immobilization aside the HRP-immobilized PANI and tested with several drops of 400 mg/dL cholesterol solutions at the same pH and dc bias, to confirm that the conductivity change of PANI only occurs via the enzymatic reaction when cholesterol oxidase is present.

FIGS. 2a, 2b, 2c, 2d, 2e, and 2f show the real time detection of 5 µl of 100 mg/dL, 150 mg/dL, 200 mg/dL, 250 mg/dL, 300 mg/dL, and 400 mg/dL water-soluble cholesterol, respectively, at a constant bias of 100 mV with fresh sensors. The current of the sensor was measured every min. Before the cholesterol solution was added on the sensor, the current was measured and showed very good stability.

When the cholesterol solution was added, within only 1 min., the current quickly decreased and stabilized, showing the fast response of the cholesterol sensor.

The fast response of the cholesterol sensor is attributed to the high reaction rates of the two enzyme reactions. In addition, because the cholesterol solution covered on both the ChOx-immobilized dialysis membrane and the HRP-immobilized PANI, the hydrogen peroxide generated from the region of the dialysis membrane needs to diffuse to the region of the HRP-immobilized PANI.

Thanks to the small volume of the cholesterol sample solution (5 µl) used in the detection, the diffusion of hydrogen peroxide did not take too long. The response time for all the concentrations of cholesterol that were tested for each measurement with fresh sensors, is less than 1 min., which is acceptable for the real application. Each concentration of cholesterol was measured with four fresh microsensors.

Figure 3A:
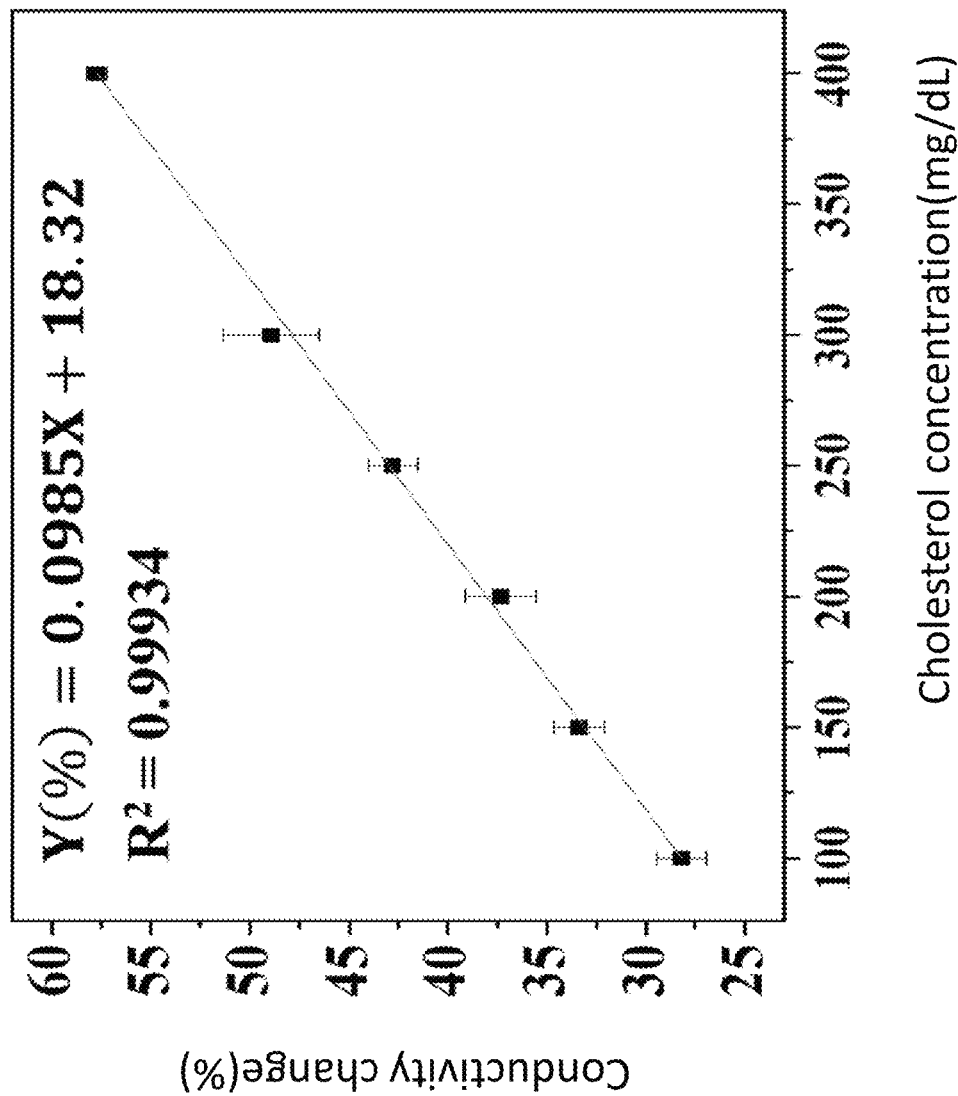
FIG. 3a shows the average percentage of conductivity changes and the error bars (standard deviation) resulted from four measurements with fresh sensors for each concentration of cholesterol, including 100 mg/dL, 150 mg/dL, 200 mg/dL, 250 mg/dL, 300 mg/dL, and 400 mg/dL as 28.17% (1.26%), 33.37% (1.23%), 37.31% (1.79%), 42.76% (1.26%), 48.92% (2.41%) and 57.72% (0.51%), respectively'

The average percentage of conductivity changes and the error bars (standard deviation) resulted from four measurements with fresh sensors for each concentration of cholesterol, including 100 mg/dL, 150 mg/dL, 200 mg/dL, 250 mg/dL, 300 mg/dL, and 400 mg/dL are shown in FIG. 3a, as 28.17% (1.26%), 33.37% (1.23%), 37.31% (1.79%), 42.76% (1.26%), 48.92% (2.41%) and 57.72% (0.51%), respectively.

The conductivity change of the microsensors shows a very good linear dependence on the cholesterol concentration, as shown in FIG. 3a, indicating a very good linearity of the sensor response. The sensitivity of this cholesterol sensor is 0.0985% per mg/dL cholesterol, which is extracted from the slope of the linear regression line fitting with the average percentage of the conductivity change versus cholesterol concentration.

The $R^2$ of the linear regression is 0.99934, indicating a very nice fitting and thereby, a reliable calibration curve. The nice linear regression fitting of the average percentage of conductivity changes and small error bars from several microsensors show the good uniformity among different sensors, indicating the great repeatability and stability of the sensor fabrication process. This result shows in the physiological cholesterol concentration, the sensor exhibits a very high sensitivity. The high sensitivity of the cholesterol microsensor is attributed to the enzymatic signal amplification by accumulating the conductivity change caused by each reactant.

Figure 3B:
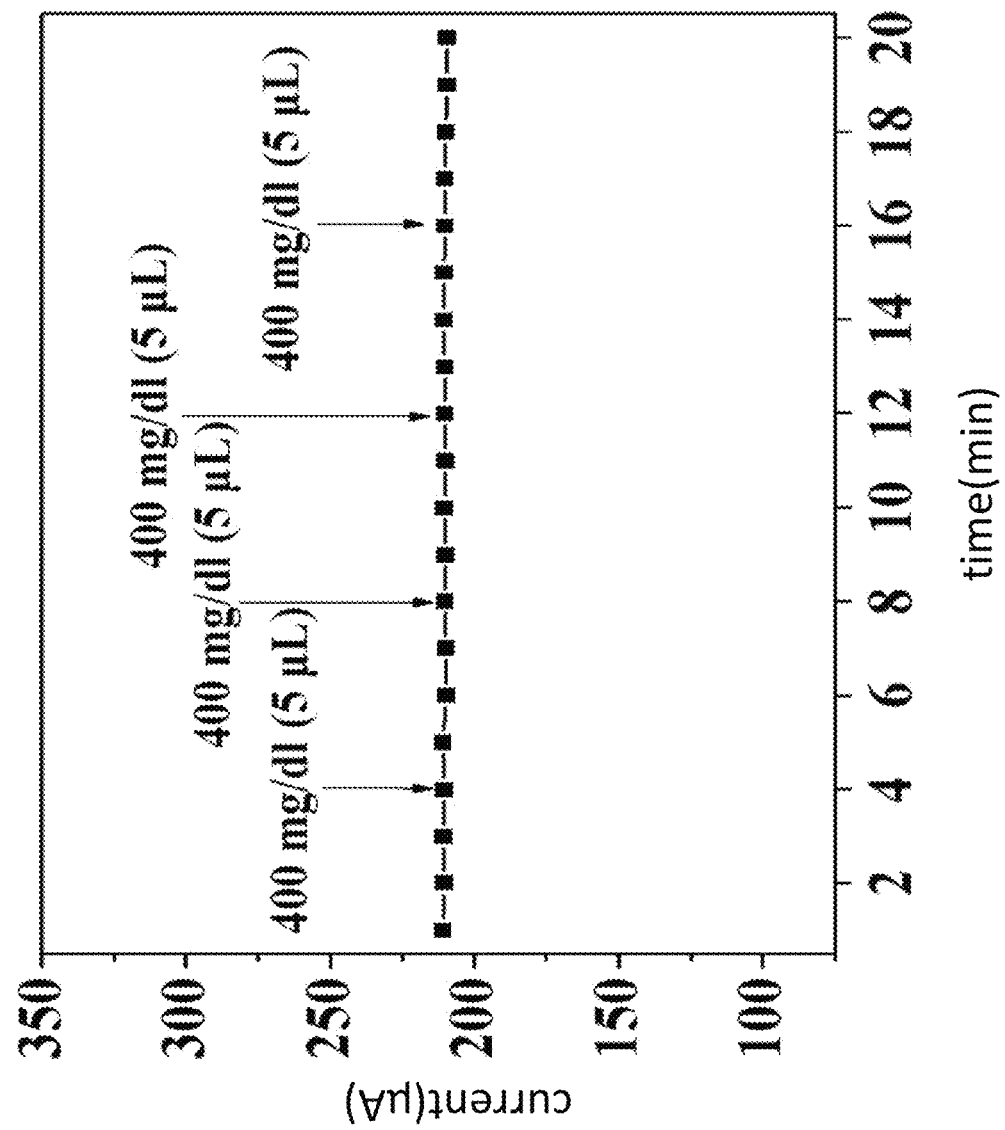
FIG. 3b shows a real-time measurement test with sensors without ChOx immobilized.

A real-time measurement was also tested with sensors without ChOx immobilized under several consecutive drops of 5 ul of 400 mg/dL cholesterol, as shown in FIG. 3b.

The results show no significant current change for every drop of the 5 ul of cholesterol solution on the sensor without ChOx immobilization, which demonstrates that the sensor does not response to cholesterol if the ChOx is not present. Thus, we can conclude that the oxidation of PANI is only occurring when CHOx and HRP are both present, therefore indicating that the enzymatic reactions are necessitated in the whole sensing process.

In summary, cholesterol oxidase-immobilized dialysis membrane and the horseradish peroxidase-immobilized conducting polymer, polyaniline, were integrated together to make a microsensor to detect cholesterol in physiological levels, ranging from 100 mg/dL to 400 mg/dL at pH=7.0. Hydrogen peroxide was produced by reaction between cholesterol and oxygen, which was catalyzed via cholesterol oxidase. The generated hydrogen peroxide further reacted with highly conductive PANI, via HRP catalysis, leading to decreased conductivity of PANI.

The resistive type sensor of the present invention has been demonstrated to be a very useful and simple platform for cholesterol detection. This cholesterol microsensor shows great current stability, fast response (less than 1 min.), high sensitivity and good linearity. The sensor also has advantages such as low cost, small size, and ease of operation, which is promising for making portable and disposable devices for routinely monitoring personal cholesterol levels.

While the invention can be subject to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:

1. A resistive sensor for an analyte, comprising:
   a substrate;
   a conductive polymer layer configured on the substrate and made of polyaniline or derivatives thereof, wherein a peroxidase is configured on the conductive polymer layer and used for oxidizing the conductive polymer layer so that a conductivity of the conductive polymer layer is decreased after applying an analyte, wherein a conductivity change of the conductive polymer layer is related to a concentration of the analyte; and
   an oxidase layer configured on the conductive polymer layer and provided with an oxidase configured thereon, wherein the oxidase is separated from the peroxidase and used for oxidizing the analyte to generate a hydrogen peroxide so that the peroxidase is oxidized by the hydrogen peroxide.

2. The resistive sensor for an analyte according to claim 1, further comprising:
   a first electrode and a second electrode, wherein the first electrode and the second electrode are electrically connected with the conductive polymer layer.

3. The resistive sensor for an analyte according to claim 2, wherein the first electrode and the second electrode are configured underneath a partial area of the conductive polymer layer.

4. The resistive sensor for an analyte according to claim 1, wherein the conductive polymer layer is pretreated with acid.

5. The resistive sensor for an analyte according to claim 1, wherein an initial current of the conductive polymer layer before applying the analyte ranges from 10 to 1000 μA at bias of 100 mV.

6. The resistive sensor for an analyte according to claim 1, wherein the surface of the conductive polymer layer is modified with propane sultone.

7. The resistive sensor for an analyte according to claim 1, wherein the oxidase layer further comprises a dialysis membrane and the oxidase is configured within the dialysis membrane.

8. The resistive sensor for an analyte according to claim 1, wherein the peroxidase comprises horseradish peroxidase, lactoperoxidase or microperoxidase.

9. The resistive sensor for an analyte according to claim 1, further comprising:
   a sensing element electrically connected to the conductive polymer layer and configured for measuring the conductivity of the conductive polymer layer.

10. The resistive sensor for an analyte according to claim 1, wherein the oxidase comprises cholesterol oxidase, glucose oxidase, alcohol oxidase or choline oxidase.

11. The resistive sensor for an analyte according to claim 1, wherein the oxidase is cholesterol oxidase.

12. The resistive sensor for an analyte according to claim 1, wherein the conductivity change of the conductive polymer layer after applying the analyte compared to before applying the analyte ranges from 10% to 60%.

13. The resistive sensor for an the analyte according to claim 1, wherein the conductivity change of the conductive polymer layer after applying the analyte compared to before applying the analyte ranges from 20% to 50%.

* * * * *